(12) United States Patent
Checa Ayet

(10) Patent No.: US 8,690,961 B2
(45) Date of Patent: Apr. 8, 2014

(54) PROSTHESIS AND METHOD FOR SURGICAL TREATMENT OF INGUINAL HERNIAS

(76) Inventor: Felix Checa Ayet, Valencia (ES)

(*) Notice: Subject to any disclaimer, the term of this patent is extended or adjusted under 35 U.S.C. 154(b) by 0 days.

(21) Appl. No.: 13/076,058

(22) Filed: Mar. 30, 2011

(65) Prior Publication Data

US 2011/0208217 A1 Aug. 25, 2011

Related U.S. Application Data

(62) Division of application No. 11/596,869, filed as application No. PCT/ES2005/000280 on May 19, 2005, now abandoned.

(30) Foreign Application Priority Data

May 19, 2004 (ES) ............................ 2004 01194 U

(51) Int. Cl.
*A61F 2/02* (2006.01)
(52) U.S. Cl.
USPC ........................................... 623/23.72
(58) Field of Classification Search
USPC ..................... 623/23.72; 606/151; 602/41
See application file for complete search history.

(56) References Cited

U.S. PATENT DOCUMENTS

| | | | | |
|---|---|---|---|---|
| 1,558,431 A | * | 10/1925 | Edward .......................... | 439/829 |
| 2,625,758 A | * | 1/1953 | Shepherd ....................... | 40/645 |
| 2,671,444 A | * | 3/1954 | Pease, Jr. ....................... | 606/151 |
| 3,482,293 A | * | 12/1969 | Kiyoshi et al. ................. | 24/543 |
| 3,604,066 A | * | 9/1971 | Moon ............................. | 24/30.5 R |
| 3,768,126 A | * | 10/1973 | Posdal ............................ | 24/561 |
| 4,324,025 A | * | 4/1982 | Apri ................................ | 24/552 |
| 5,116,357 A | * | 5/1992 | Eberbach ....................... | 606/213 |
| 5,122,155 A | * | 6/1992 | Eberbach ....................... | 606/213 |
| 5,141,515 A | * | 8/1992 | Eberbach ....................... | 606/151 |
| 5,147,374 A | * | 9/1992 | Fernandez ..................... | 606/151 |
| 5,356,432 A | * | 10/1994 | Rutkow et al. ............... | 623/23.72 |
| 5,366,460 A | * | 11/1994 | Eberbach ....................... | 606/151 |
| 5,425,740 A | * | 6/1995 | Hutchinson, Jr. ............. | 606/157 |
| 5,495,645 A | | 3/1996 | Suzuki et al. ................. | 24/30.5 S |

(Continued)

FOREIGN PATENT DOCUMENTS

| EP | 0 628 292 | 12/1994 |
|---|---|---|
| EP | 0628292 | 1/1997 |

(Continued)

OTHER PUBLICATIONS

Cirugia y Cirujanos, Nov.-Dec. 2002, vol. 70, No. 6, pp. 422-427 (2002).

*Primary Examiner* — Corrine M McDermott
*Assistant Examiner* — Son Dang
(74) *Attorney, Agent, or Firm* — Berenato & White, LLC

(57) ABSTRACT

A method for surgical treatment of inguinal hernias includes the steps of providing a surgical prosthesis in the form of a laminar component having an approximately intermediate cut line forming two asymmetrical halves each having at a distal end thereof an end tab, and overlaying the asymmetrical halves of the laminar component by superimposing the end tabs of the asymmetrical halves so as to form two reinforced triangular areas aligned with anatomically weak areas of the patient and to create a central through cavity so that a spermatic cord of the patient extends through the central through cavity. The surgical prosthesis is intended to protect weak points in an abdominal wall of the patient.

19 Claims, 2 Drawing Sheets

(56) References Cited

U.S. PATENT DOCUMENTS

| | | | |
|---|---|---|---|
| 5,972,007 A * | 10/1999 | Sheffield et al. | 606/151 |
| 6,257,241 B1 * | 7/2001 | Wampler | 128/898 |
| 6,258,124 B1 | 7/2001 | Darois et al. | 623/14 |
| 6,287,344 B1 | 9/2001 | Wampler et al. | 623/23.72 |
| 6,293,956 B1 * | 9/2001 | Crainich et al. | 606/155 |
| 6,513,767 B1 * | 2/2003 | Rodgers | 248/74.2 |
| 6,610,006 B1 | 8/2003 | Amid et al. | |
| 6,765,122 B1 * | 7/2004 | Stout | 602/41 |
| 6,849,057 B2 * | 2/2005 | Satou et al. | 602/75 |
| 7,094,261 B2 * | 8/2006 | Zotti et al. | 623/23.72 |
| 7,381,225 B2 * | 6/2008 | Croce et al. | 623/23.72 |
| 2003/0171823 A1 | 9/2003 | Zotti et al. | |
| 2004/0092937 A1 | 5/2004 | Criscuolo et al. | 606/72 |
| 2005/0119677 A1 * | 6/2005 | Shipp | 606/157 |
| 2006/0129168 A1 * | 6/2006 | Shipp | 606/151 |

FOREIGN PATENT DOCUMENTS

| | | |
|---|---|---|
| EP | 1 060 714 | 12/2000 |
| EP | 1060714 | 8/2006 |
| ES | 2163485 | 2/2002 |

\* cited by examiner

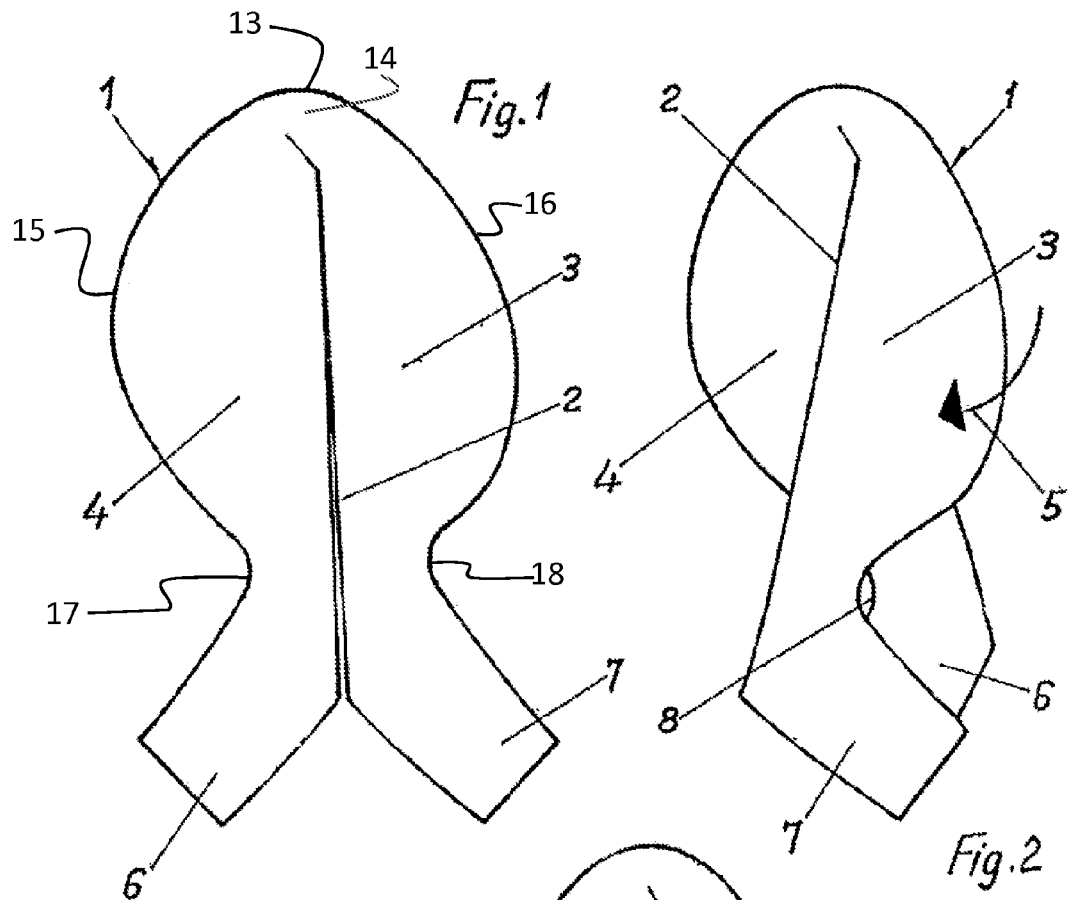
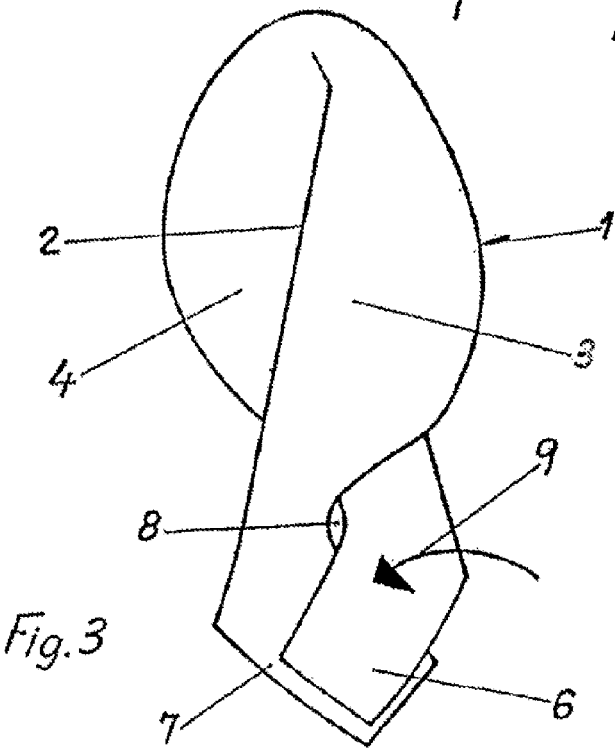

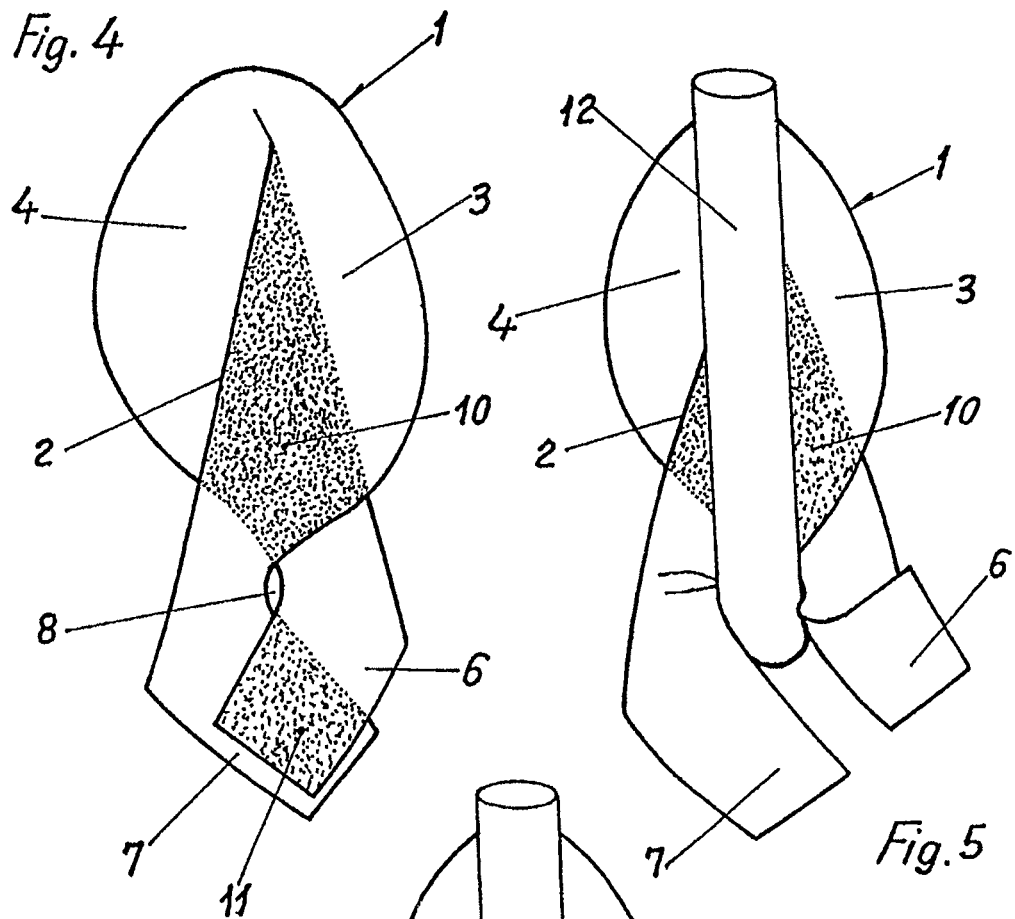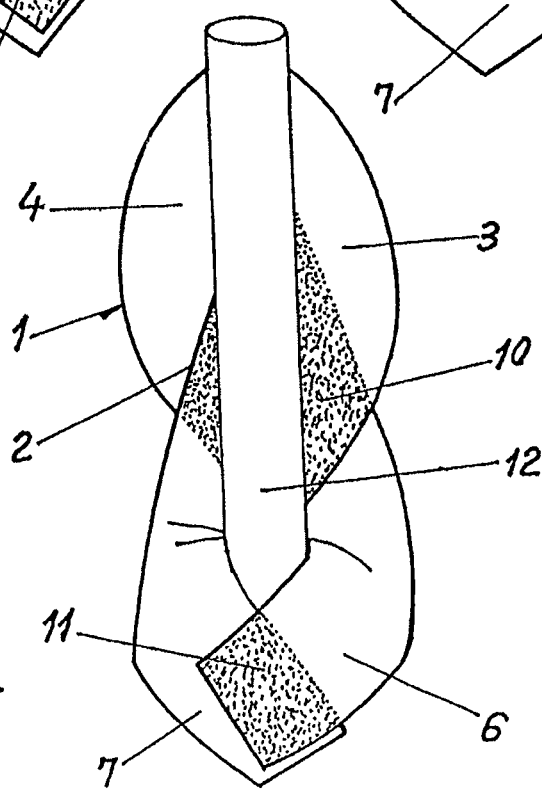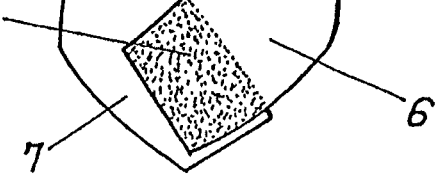

PROSTHESIS AND METHOD FOR SURGICAL TREATMENT OF INGUINAL HERNIAS

CROSS-REFERENCE TO RELATED APPLICATIONS AND CLAIM TO PRIORITY

This application is a divisional of U.S. application Ser. No. 11/596,869 filed Nov. 17, 2006, which has been abandoned, which claims priority to PCT/ES05/000280 filed May 19, 2005, both of which are incorporated herein by reference in their entirety.

FIELD OF THE INVENTION

The object of the present invention corresponds to a surgical prosthesis for the treatment of inguinal hernia, having been obtained in its structuring of a new conception taking on the form of a loop and whose design is based to the utmost on the anatomical constitution (which is altered in the case of hernias) of the human body in order to protect the weak spots of the abdominal wall such as the internal orifice and the whole posterior wall of the inguinal duct, so that the loop prosthesis to which we have been referring sets out to resolve by means of a single prosthetic piece the two most common types of inguinal hernias with the maximum safety and efficacy.

BACKGROUND OF THE INVENTION

The current technique contemplates the existence of various prostheses for the surgical treatment of inguinal hernias, normally made in different materials such as polypropylene or Goretex, offering various designs and features, but we consider that all the systems used do not achieve the desired degree of efficacy and for this purpose we have studied and created the improved prosthesis at hand here, in which its "loop" type design improves surgical results sensibly, this prosthesis being on the other hand quite different from the various means currently used.

SUMMARY OF THE INVENTION

Essentially the improved prosthesis for the surgical treatment of hernias of the groin that is the object of the present registration stems from a flat surface which presents a middle bisecting line separating two asymmetric halves, the first part of the loop being formed with the right half superimposed over the left, the bow being finally formed by the lower tabs, with the right-hand tab being superimposed on the left-hand one. In this way, with the first part of the "loop" already made, it encircles the spermatic cord whose posterior wall it is aimed to reinforce, as well as the anatomical ring through which this cord emerges, which it surrounds forming an artificial ring, enlarging the areas of increased resistance, which match up with the anatomical areas whose alteration gives rise to the appearance of the most common forms of inguinal hernias.

On account of its helical development the "loop" prosthesis configuration presents a dynamic aspect as it restrains the movements of the muscles to which it is attached and remains fixed.

The figures represented in the drawings attached show as specified below:

FIG. 1.—Front development view of the plane morphology piece of the prosthesis, wherein there is a middle bisecting line partly separating two asymmetric halves with which the loop is formed.

FIG. 2.—Front view of the piece in FIG. 1, with the first phase for forming the loop with the right-hand part overlying the left-hand half, as may be observed according to the direction of the superimposed directional arrow.

FIG. 3.—Front view of the piece of FIGS. 1 and 2 with the termination of the bow in accordance with the superimposed arrow, with the lower superimposed tabs forming the bow, with the result that the tab of the left-hand half overlies the tab of the right-hand half, leaving a minimised central cavity which will accommodate the spermatic cord snugly in the form of an anatomic ring.

FIG. 4.—Front view of the folded laminar piece forming the loop, showing the areas of increased strength achieved (dotted), corresponding to two triangular areas, arranged to match up with the patient's anatomically weak areas.

FIG. 5.—Front view of FIG. 4, where the development diagram of the prosthesis may be observed with the first portion of the loop already made and the incorporation of the spermatic cord within the loop obtained by means of the raising of the superimposed lower tab of the left-hand half.

FIG. 6.—The same front view of FIGS. 4 and 5, showing how it encircles the spermatic cord, whose posterior wall it is intended to reinforce, as well as the anatomical ring through which said cord emerges, which it ensheathes forming an artificial ring, whilst the areas of increased strength may also be observed, matching up with the anatomical areas whose alteration brings about the appearance of the most common forms of inguinal hernias.

DETAILED DESCRIPTION OF THE INVENTION

Referring always to the attached diagrams, it should be pointed out that in the different figures represented in them numerical elevational values have been included relating to the descriptions of its features and operation that are set out hereinunder, in this way facilitating their immediate localisation, (1) being a front development view of the laminar piece that will form the loop, having a bisecting line (2) executed more or less down the center, partly dividing the piece (1) into two asymmetric halves, the right-hand side half (or the first side portion) (3) and the other left-hand side half (or the second side portion) (4), between which two halves the loop will be formed for the surgical treatment of hernias of the groin. The bisecting line (2) terminates below the top edge (13) of the piece (1), so that the right-hand side half (3) and the left-hand side half (4) are connected to one another by a connecting portion (14) above the top of the bisecting line (2). The right-hand side half (3) and the left-hand side half (4) have outer edges (15) and (16), respectively. The outer edges (15) and (16) have convexities below the top edge (13), then transition to concavities which extend inwardly towards the bisecting line (2) then outwardly at lower end tabs (6) and (7), respectively. The concavities of the outer edges (15) and (16) define continuously curved grooves (17) and (18), respectively, which are opposite to one another in FIG. 1.

In FIG. 2 it may be seen how the first part of the loop is formed with the right-hand side (3) overlying the left-hand half (4), as indicated by the direction of the arrow (5), the bow being finally formed, as may be observed in FIG. 3, with the result that the lower end tab (6) of the left-hand side (4) is superimposed on the lower end tab (7) of the right-hand side (3). The overlaying operation (5) discussed above places the grooves (17) and (18) numbered in FIG. 1 in facing relationship to one another to form a central cavity (8). The superimposing operation is performed as indicated by the directional arrow (9) which determines the positioning.

According to the folding of the pieces of the loop in accordance with the process shown in FIGS. 2 and 3, we may observe the areas of increased strength obtained, corresponding to two triangular areas (10 and 11), represented with dots, in the areas of superimposition of two pieces of the loop, which are made to match up with the patient's anatomically weak areas.

In the central cavity (8), obtained by the installation of the two right-hand and left-hand parts (8 and 9) respectively of the general piece, the spermatic cord (12) will be fitted by raising the tab (6), the spermatic cord being ensheathed over the area corresponding to the posterior wall which it is intended to reinforce, as well as the anatomical ring through which there emerges said cord, which it encircles forming an artificial ring.

As may be observed in FIG. 6, the areas of increased strength match up with the anatomical areas whose alteration brings about the appearance of the most common forms of inguinal hernias.

The design of the prosthesis (1) is based on the normal anatomical constitution, with the prosthesis forming a loop in order to remedy the weak areas which give rise to the two most common forms of inguinal hernias with a single prosthetic piece, with the result that on account of its helical development the "loop" prosthesis presents a dynamic configuration, which restrains the movements of the muscles to which it is attached and fixed.

Considering amply described each and every one of the parts making up the improved prostheses for the surgical treatment of groin hernias which is the object of the invention, it only remains for us to state the possibility that the different parts may be made in a variety of materials, sizes and shapes, while those variations of a constructional type as advocated by practice may also be incorporated into its constitution, providing that they are not capable of altering the essential points of what is the object of the present Utility Model registration.

The invention claimed is:

1. A method for surgical treatment of inguinal hernias of a patient, comprising the steps of:
    providing a surgical prosthesis in the form of a laminar component comprising an approximately intermediate cut line forming two asymmetrical halves of said laminar component, each of said asymmetrical halves having at a distal end thereof an end tab;
    overlaying said asymmetrical halves of said laminar component by superimposing said end tabs of said asymmetrical halves so as to form two reinforced triangular areas aligned with anatomically weak areas of the patient and to create a central through cavity forming a ring adapted to encircle a spermatic cord of the patient extending through said central through cavity; and
    fitting the spermatic cord in the central through cavity,
    wherein the step of overlaying said asymmetrical halves and superimposing said end tabs creates a helical conformation establishing said two reinforced triangular areas that restrain the movements of muscles of the patient so as to permit treatment of two most common types of the inguinal hernias with a single prosthesis, and
    wherein each of said two symmetrical halves has a respective outer edge with a concavity extending inwards towards said approximately intermediate cut line to define a curved groove, wherein said steps of overlaying and fitting causes said curved grooves of said two symmetrical halves to face one another to form said central through cavity.

2. The method of claim 1, wherein said laminar component further comprises a connecting portion above said cut line to connect said asymmetrical halves to one another.

3. The method of claim 1, wherein said step of overlaying positions said two reinforced triangular areas on opposite sides of the spermatic cord.

4. The method of claim 3, wherein said step of overlaying comprises placing a first of said asymmetrical halves on a second of said asymmetrical halves at a first of said two reinforced triangular areas, and superimposing said second of said asymmetrical halves on said first of said asymmetrical halves at a second of said two reinforced triangular areas.

5. The method of claim 1, wherein said curved grooves are continuous curves.

6. A method for surgical treatment of inguinal hernias of a patient, comprising the steps of:
    treating an inguinal hernia of a patient with a surgical prosthesis in the form of a laminar component comprising a first side portion, a second side portion, and an approximately intermediate bisecting line between the first side portion and the second side portion, the first side portion having a first outer edge with a first concavity extending inward towards the approximately intermediate bisecting line to define a first curved groove, the second side portion having a second outer edge with a second concavity extending inward towards the approximately intermediate bisecting line to define a second curved groove that is opposite to the first curved groove, the first and second side portions comprising first and second distal end tabs, respectively,
    said treating comprising overlaying the first side portion and the second side portion with one another in a helical conformation and fitting a spermatic cord of the patient in the helical conformation so that the first and second distal end tabs are superimposed and so that the first and second curved grooves face one another to establish a through cavity about the spermatic cord extending through the through cavity, said overlaying and said fitting establishing first and second reinforced areas on opposite sides of the spermatic cord.

7. The method of claim 6, wherein the laminar component further comprises a connecting portion above the approximately intermediate bisecting line to connect the first and second side portions to one another.

8. The method of claim 6, wherein said overlaying comprises placing the first side portion on the second side portion at the first reinforced area and superimposing the second distal end tab of the second side portion on the first distal end tab of the first side portion at the second reinforced area.

9. The method of claim 6, wherein the first and second concavities are each continuously curves.

10. The method of claim 6, wherein the through cavity is in the form of a ring.

11. The method of claim 6, wherein the first outer edge comprises a first convexity extending from a top edge of the laminar component to the first concavity, and wherein the second outer edge comprises a second convexity extending from the top edge of the laminar component to the second concavity.

12. The method of claim 6, wherein the first and second reinforced areas are triangular.

13. The method of claim 6, wherein the first and second reinforced areas are aligned with anatomically weak areas of the patient.

14. The method of claim 13, wherein the first and second reinforced areas restrain movement of muscles of the patient so as to permit treatment of two most common types of the inguinal hernias with a single prosthesis.

15. The method of claim 14, wherein the first outer edge comprises a first convexity extending from a top edge of the laminar component to the first concavity, and wherein the second outer edge comprises a second convexity extending from the top edge of the laminar component to the second concavity.

16. The method of claim 14, wherein the first and second reinforced areas are aligned with anatomically weak areas of the patient.

17. The method of claim 16, wherein the first and second reinforced areas restrain movement of muscles of the patient so as to permit treatment of two most common types of the inguinal hernias with a single prosthesis.

18. A method for surgical treatment of inguinal hernias of a patient, comprising the steps of:

treating an inguinal hernia of a patient with a surgical prosthesis in the form of a laminar component comprising a first side portion, a second side portion, an approximately intermediate bisecting line between the first side portion and the second side portion, and a connecting portion above the approximately intermediate bisecting line to connect the first and second side portions to one another, the first side portion having a first outer edge with a first concavity extending inward towards the approximately intermediate bisecting line to define a first curved groove, the second side portion having a second outer edge with a second concavity extending inward towards the approximately intermediate bisecting line to define a second curved groove that is opposite to the first curved groove, the first and second side portions comprising first and second distal end tabs, respectively, said treating comprising overlaying the first side portion and the second side portion with one another in a helical conformation and fitting a spermatic cord of the patient in the helical conformation so that the first and second curved grooves face one another to establish a through cavity about the spermatic cord extending through the through cavity with first and second reinforced areas on opposite sides of the spermatic cord, the first reinforced area having the first side portion overlaying the second side portion, the second reinforced area having the second distal end tab superimposed on the first distal end tab.

19. The method of claim 18, wherein the first and second concavities are each continuously curves.

\* \* \* \* \*